(12) United States Patent
Ouchi et al.

(10) Patent No.: US 6,514,197 B1
(45) Date of Patent: Feb. 4, 2003

(54) TREATMENT TOOL SUPPORT DEVICE FOR ENDOSCOPE

(75) Inventors: Teruo Ouchi, Saitama (JP); Masaru Nagamine, Kagawa (JP)

(73) Assignee: Pentax Corporation, Tokyo (JP)

( * ) Notice: Subject to any disclaimer, the term of this patent is extended or adjusted under 35 U.S.C. 154(b) by 73 days.

(21) Appl. No.: 09/688,877

(22) Filed: Oct. 17, 2000

(30) Foreign Application Priority Data

Oct. 18, 1999 (JP) .......................................... 11-294682

(51) Int. Cl.[7] ................................................ A61B 1/00
(52) U.S. Cl. ...................... 600/106; 600/104; 600/127; 600/129
(58) Field of Search ................................ 600/106, 104, 600/105, 107, 127, 129

(56) References Cited

U.S. PATENT DOCUMENTS

| | | | | |
|---|---|---|---|---|
| 4,982,727 A | * | 1/1991 | Sato ............................ | 600/104 |
| 5,014,708 A | * | 5/1991 | Hayashi et al. ............... | 600/105 |
| 5,035,248 A | * | 7/1991 | Zinnecker .................... | 600/564 |
| 5,417,203 A | * | 5/1995 | Tovey et al. ................. | 600/106 |
| 5,578,056 A | * | 11/1996 | Pauldrach .................... | 606/205 |
| 5,865,724 A | * | 2/1999 | Palmer et al. ............... | 600/104 |
| 5,882,293 A | * | 3/1999 | Ouchi .......................... | 600/104 |
| 5,904,647 A | * | 5/1999 | Ouchi .......................... | 600/104 |
| 6,013,095 A | | 1/2000 | Ouchi | |
| 6,066,102 A | * | 5/2000 | Townsend et al. ........... | 600/104 |

FOREIGN PATENT DOCUMENTS

| | | |
|---|---|---|
| JP | 5-54345 | 8/1993 |
| JP | 9-276285 | 10/1997 |
| JP | 10-24045 | 1/1998 |

\* cited by examiner

*Primary Examiner*—Linda C. M. Dvorak
*Assistant Examiner*—Kenneth Schopfer
(74) *Attorney, Agent, or Firm*—Greenblum & Bernstein, P.L.C.

(57) ABSTRACT

A treatment tool support device comprises a moving mechanism support member and a sheath connecting cap. The moving mechanism support member is manufactured by bending a plate in such a manner that a first bottom portion defining a part of a support groove is formed. A treatment tool moving mechanism for moving a biopsy forceps is supported. The sheath connecting cap is provided on an end portion of a sheath, in which an operating member for operating the biopsy forceps is provided. The sheath connecting cap is manufactured by deep drawing such as press molding. The first bottom portion of the moving mechanism support member is connected to a second bottom of the sheath connecting cap through crimping, welding or brazing.

7 Claims, 8 Drawing Sheets

TREATMENT TOOL SUPPORT DEVICE FOR ENDOSCOPE

BACKGROUND OF THE INVENTION

1. Field of the Invention

The present invention relates to a treatment tool, which is inserted through a treatment tool insert channel of an endoscope and used for an operation within a body.

2. Description of the Related Art

Figure 1:
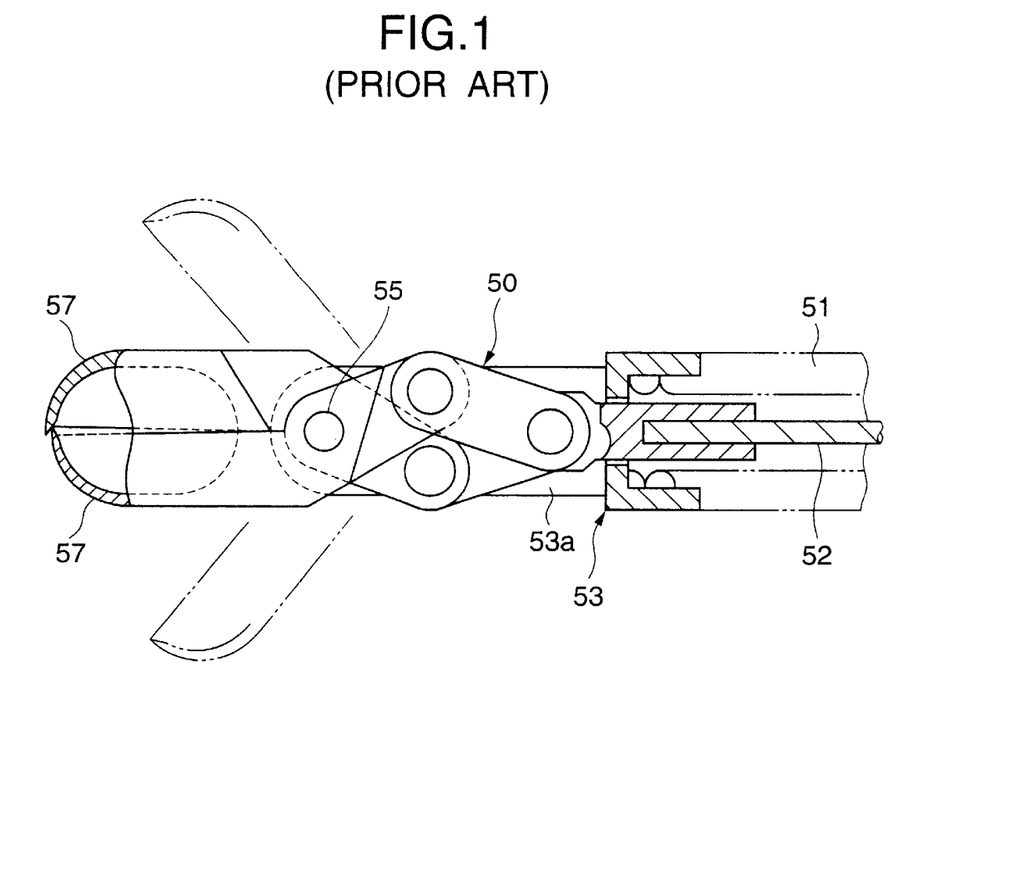
FIG. 1 is a side view, partly sectioned, showing an end portion of a biopsy forceps of an endoscope in a prior art.

FIG. 1 shows an end portion of a biopsy forceps which is a typical treatment tool of an endoscope. As shown in the drawing, an operating wire 52 is inserted in a flexible sheath 51 and is movable along the longitudinal axis of the sheath 51. A pair of forceps cups 57 is pivoted on an end support unit 53 attached to an end portion of the sheath 51, and is opened and closed like a beak.

The end support unit 53 is provided with a groove 53a, which is open at the end side of the end support unit 53. In the groove 53a, a moving mechanism 50 is provided and moved by an operating wire 52 to open and close the forceps cups 57.

Figure 2:
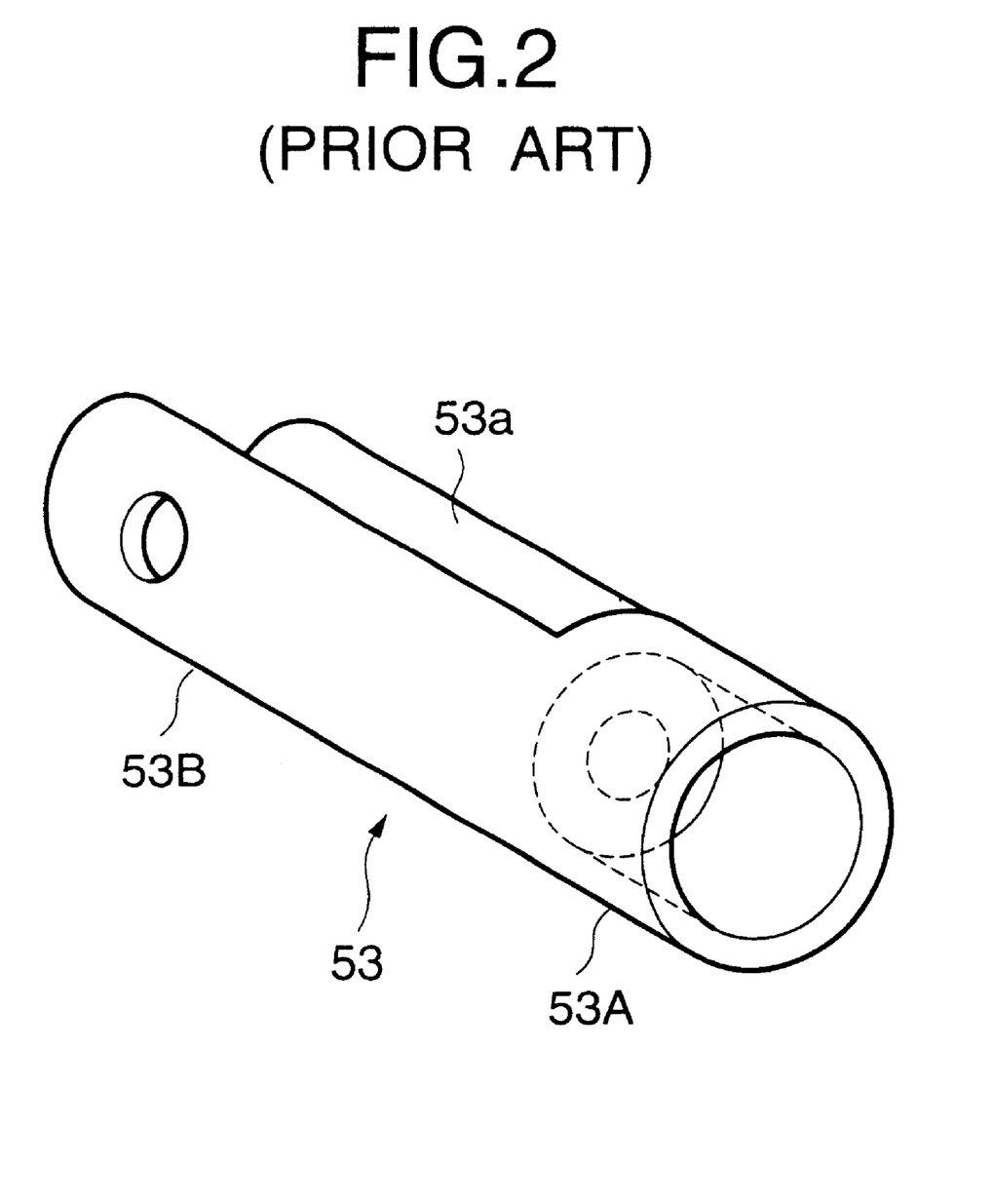
FIG. 2 is a perspective view showing an end support member of the prior art.

FIG. 2 shows the end support unit 53. As shown in the drawing, a rear-end portion 53A of the end support unit 53 is cylindrically formed so that an end portion of the sheath 51 can be inserted therein. A front-end portion 53B of the end support unit 53 is provided with the groove 53a in which the moving mechanism 50 is disposed as described above.

Accordingly, for manufacturing the end support unit 53, it is necessary that one end portion of a rod-shaped material is drilled to form a bore and another end portion of the rod-shaped material is cut to form the groove 53a. Thus, two cutting processes are required, in which a machine such as a milling machine is used, and therefore, the manufacturing cost of the end support unit 53 is high.

SUMMARY OF THE INVENTION

Therefore, an object of the present invention is to provide a treatment tool support device for an endoscope, which can be manufactured at a relatively low cost.

According to the present invention, there is provided a treatment tool support device provided in an endoscope for supporting a treatment tool, the device comprising a moving mechanism support member, a sheath connecting cap and a connecting means.

The moving mechanism support member has a support groove in which a treatment tool moving mechanism is supported. The moving mechanism support member is manufactured by bending a plate in such a manner that a first bottom portion defining a part of the support groove is formed. The first bottom portion is provided with a firsthole. The sheath connecting cap is provided on an end portion of a sheath, in which an operating member for driving the treatment tool moving mechanism is provided. The sheath connecting cap has a second bottom portion provided with a second hole. The connecting means connects the moving mechanism support member and the sheath connecting cap in such a manner that the first bottom portion and the second bottom portion are fixed to each other and the treatment tool moving mechanism and the operating member are connected through the first and second holes.

Preferably, each of the moving mechanism support member and the sheath connecting cap is manufactured by a press molding. Further, the first bottom portion and the second bottom portion may be fixed to each other by one of crimping, welding and brazing. Thus, the manufacturing cost can be further reduced.

The moving mechanism support member and the sheath connecting cap are connected to each other such that the first and second holes are aligned with each other, so that a connecting member connecting the operating member to the treatment tool moving mechanism is positioned in the first and second holes.

The sheath may have a corrugated outer surface and the sheath connecting cap may have a corrugated inner surface which is formed in conformity with the corrugated outer surface. Thus, the sheath connecting cap can be tightly connected to the sheath.

Furthermore, according to the present invention, there is provided a treatment tool support device provided in an endoscope for supporting a treatment tool, the device comprising a moving mechanism support member and a sheath connecting member.

The moving mechanism support member has a support groove in which a treatment tool moving mechanism for moving the treatment tool is supported. The moving mechanism support member is manufactured by bending a plate so as to form the support groove. The sheath connecting member is provided on an end portion of a sheath. The sheath connecting member is manufactured from a tube to be a cap-shape having a hole on the axis thereof. The sheath connecting member is integrated to the moving mechanism support member.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

The present invention will be described below with reference to the embodiments shown in the drawings.

Figure 3:
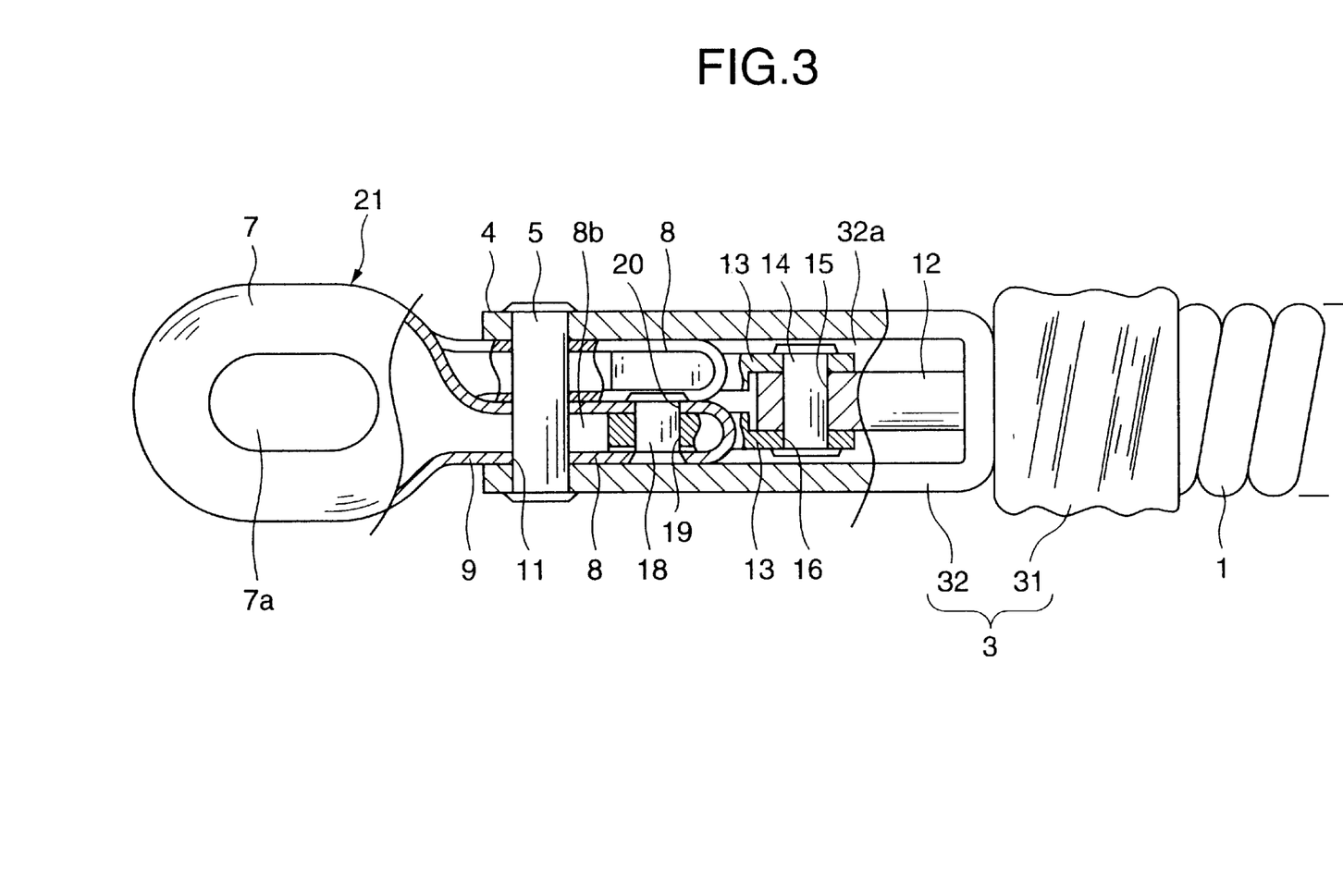
FIG. 3 is a plan view, partly sectioned, of an end portion of a biopsy forceps of an endoscope, to which an embodiment of the present invention is applied, and in which the biopsy forceps is closed.
Figure 4:
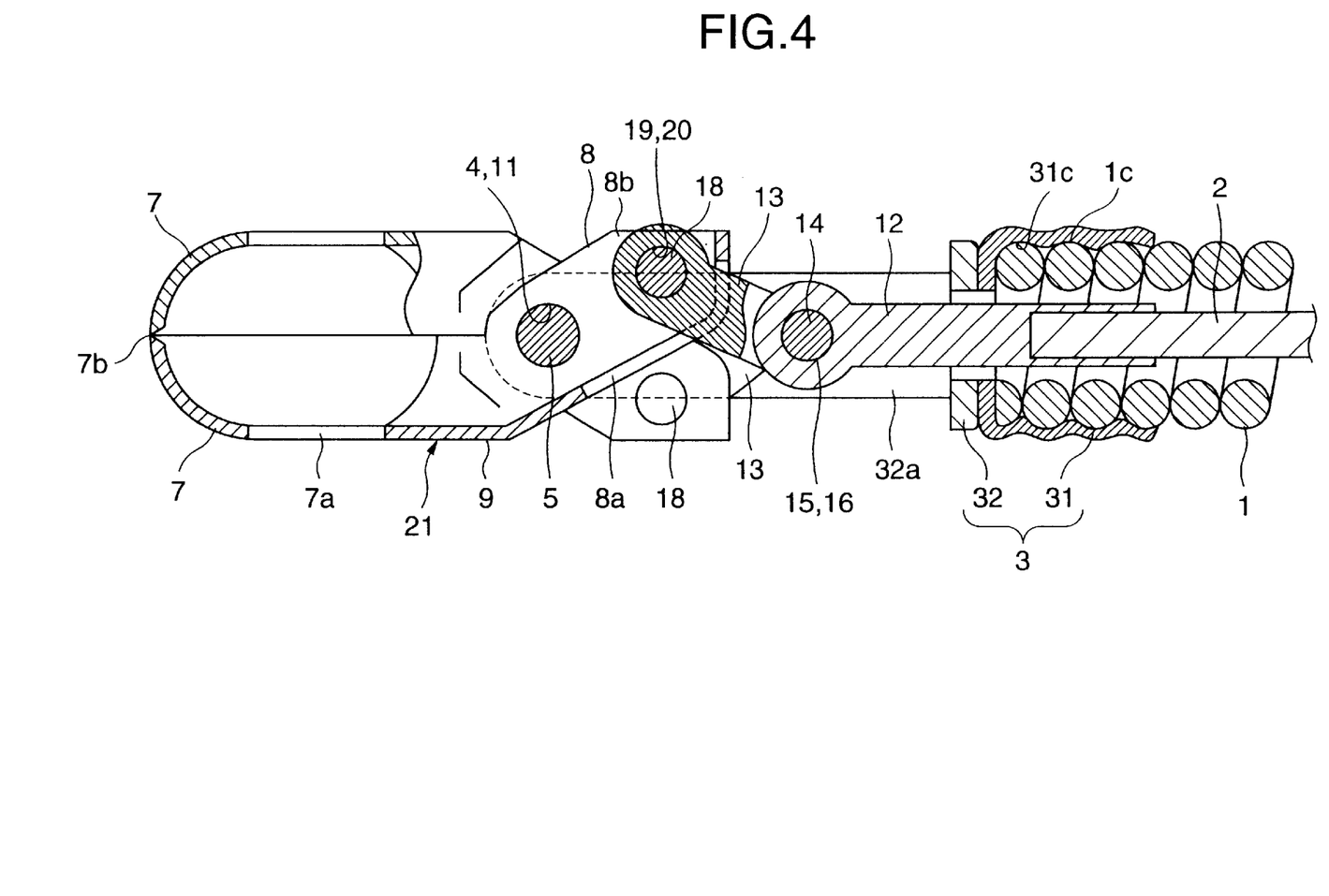
FIG. 4 is a side view, partly sectioned, of the end portion of the biopsy forceps, which is closed.

FIGS. 3 and 4 show an end portion of a biopsy forceps of an endoscope, to which an embodiment of the present invention is applied. FIG. 3 is a partially sectioned plan view and FIG. 4 is a partially sectioned side view. Note that, in each of FIGS. 3 and 4, different parts are sectioned so that the constructions of the biopsy forceps can be explained with fewer drawings.

A flexible sheath 1, which is inserted in a forceps channel (not shown) of the endoscope, is a tightly wound tube, which is formed by winding a stainless steel, for example, in such a manner the stainless steel forms a tube with a constant diameter and adjacent portions of the steel come in contact each other. The tightly wound tube of the sheath 1 may be have a flexible covering, or some other construction. The length of the sheath 1 is approximately 1 to 2.5 m and the diameter of the sheath 1 is approximately 1.5 to 3 mm, for example.

An operating wire 2 is provided in the sheath 1. The operating wire 2 extends within the whole length of the sheath 1, and is movable along the axial direction of the sheath 1. A rear end portion (not shown) of the operating wire 2 is connected to an operating unit (not shown), by which the operating wire 2 is moved.

Figure 5:
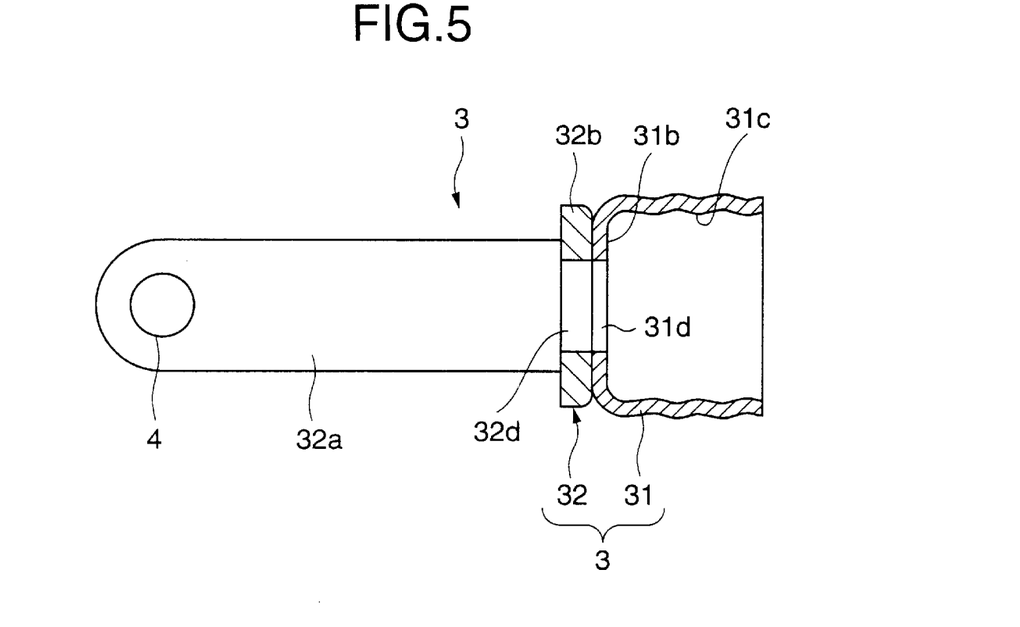
FIG. 5 is a view showing only an end support unit in assembled condition.
Figure 6:
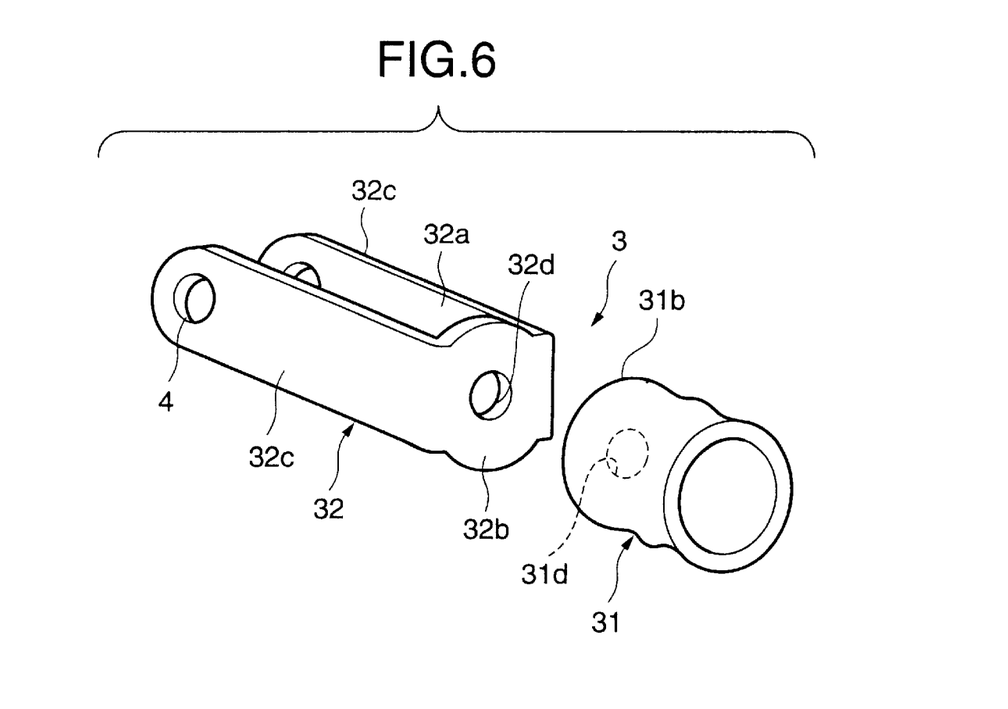
FIG. 6 is a view showing only the end support unit in disassembled condition.

An end support unit 3 is fixed to an end portion of the sheath 1. FIG. 5 shows only the end support unit 3 in assembled condition and FIG. 6 shows the end support unit 3 in disassembled condition. As understood from these drawings, the end support unit 3 has a sheath connecting cap 31 and a moving mechanism support member 32. The sheath connecting cap 31 is connected to an end portion of the sheath 1. The moving mechanism support member 32 has a first bottom portion 32b, to which a second bottom portion 31b of the sheath connecting cap 31 is fixed or connected by spot welding or silver brazing, for example, so that the sheath connecting cap 31 and the moving mechanism support member 32 are integrated with each other.

The sheath connecting cap 31 is made from a metal tube, such as a stainless steel tube, to be a cap-shape having a hole on the axis thereof, or manufactured from stainless steel by deep drawing such as press molding. The sheath connecting cap 31 has a corrugated inner surface, which is spiral, so that the sheath connecting cap 31 is threadingly fitted on the end portion of the sheath 1. Namely, the corrugated inner surface 31c is in conformity with a corrugated outer surface 1c (FIG. 2) of the sheath 1.

The moving mechanism support member 32 is manufactured by bending a plate, using press molding, in such a manner that the first bottom portion 32b and side walls 32c are formed. Thus, a support groove 32a is defined by the first bottom portion 32b and the side walls 32c.

The first bottom portion 32b of the moving mechanism support member 32 is provided with a first hole 32d, and the second bottom portion 31b of the sheath connecting cap 31 is provided with a second hole 31d. The first bottom portion 32b and the second bottom portion 31b are connected to each other such that the first and second holes 32d and 31d are aligned with each other. A wire connecting link 12, connecting the operating wire 2 to a treatment tool moving mechanism 10, described later, is loosely fitted in the first and second holes 32d and 31d.

Thus, the end support unit 3 can be manufactured using substantially only press molding and cutting processes using a milling machine and so on do not need to be performed. Therefore, the manufacturing cost of the end support unit 3 can be drastically reduced.

A pin support hole 4 is formed in an end portion of each of the side walls 32c. The pin support holes 4 penetrate the side walls 32c, and extend in a direction perpendicular to the longitudinal direction of the moving mechanism support member 32. The axes of the pin support holes 4 are aligned, and a support pin 5 is inserted in the pin support holes 4. Both ends of the support pin 5 project from the side walls 32c, and the projecting portions are formed so that the support pin 5 is fixed to the side walls 32c, as shown in FIG. 3.

A treatment tool is composed of biopsy forceps 21, each of which is provided with a forceps cup 7 and an operating lever 8, which are integrally formed. The biopsy forceps 21 are rotatably supported by the support pin 5. The forceps cups 7 project from the end support unit 3 as shown in FIGS. 3 and 4 and an opening of each of the forceps cups 7 faces each other.

Figure 7:
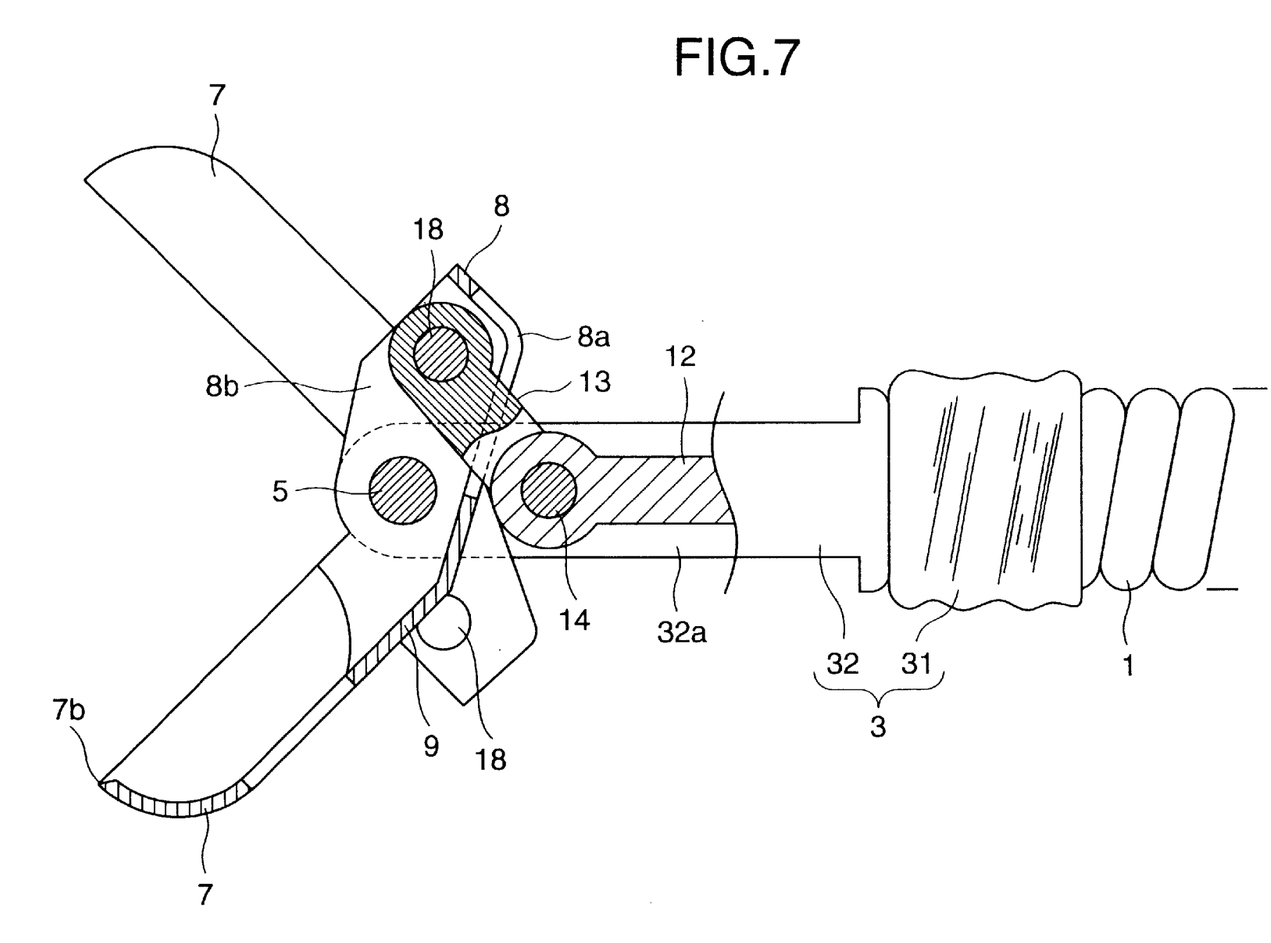
FIG. 7 is a side view, partly sectioned, of the end portion of the biopsy forceps, which is open.

The operating levers 8 are positioned in the support groove 32a, and the support pin 5 is inserted through a hole 11 formed in each of the operating levers 8. Namely, the operating levers 8 are rotatable about the support pin 5, so that the forceps cups 7 are opened and closed like a beak. Note that FIG. 7 shows a state in which the forceps cups 7 are open.

Figure 8:
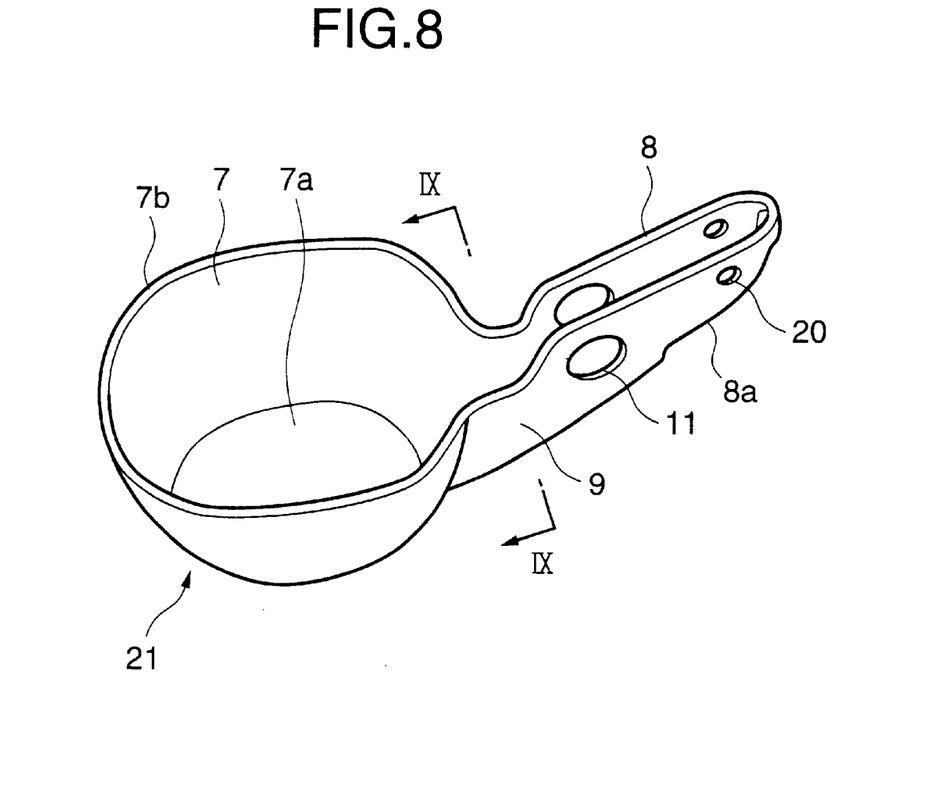
FIG. 8 is a perspective view showing a member of the biopsy forceps, in which a forceps cup and an operating lever are formed as one body.

FIG. 8 shows a part of the biopsy forceps 21. The forceps cup 7 and the operating lever 8 are manufactured from a sheet of stainless steel by press molding, and are like a spoon having a short stem as a whole. The forceps cup 7 is a long semi-sphere, and has a hole 7a at a bottom portion. A cutting blade 7b is formed along an inner periphery of the opening.

Figure 9:
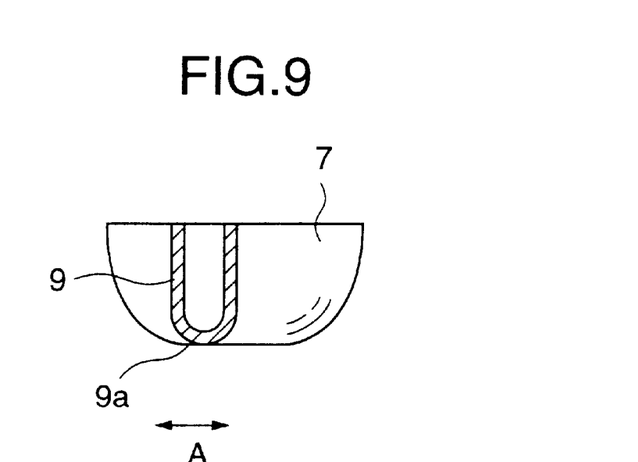
FIG. 9 is a sectional view along IX—IX line of FIG. 8.

As shown in FIG. 8, a boundary portion 9 between the forceps cup 7 and the operating lever 8 is formed in an approximately U-shaped section and the operating lever 8 has a U-shaped section continuing to the boundary portion 9. Thus, in the U-shaped section, the bottom portion 9a of the U-shape works as a beam resisting a lateral force, the direction of which is shown by an arrow A in FIG. 9, so that excellent strength is obtained.

An end portion of the wire connecting link 12, connected to the end portion of the operating wire 2, is positioned in the support groove 32a of the moving mechanism support member 32. Two link plates 13, sandwiching the end portion of the wire connecting link 12, are rotatably connected to the end portion of the wire connecting link 12 by a rivet 14.

The rivet 14 is loosely and rotatably fitted in a hole formed in the wire connecting link 12, and both end portions of the rivet 14, projecting from the link plates 13, are formed over.

A groove 8b is formed in the operating lever 8 having the U-shaped section, and is extended perpendicular to the support pin 5. Another end portion of each of the link plates 13 is inserted in the groove 8b, and is rotatably connected to the operating lever 8 with a rivet 18, respectively. Both end portions of each of the rivets 18 are held by the operating lever 8.

The two rivets 18 are loosely and rotatably fitted in holes 19 formed in the link plates 13 and both end portions of each of the rivets 18 are supported by holes 20 formed in each of the operating levers 8. Note that a slot 8a is formed in each of the bottom portions of the operating levers 8 so that each of the link plates 13 passes through the slot 8a and is connected to the rivet 18.

Thus, the wire connection link 12, the two link plates 13, and the operating lever 8 form a link mechanism, having a pantograph shape, which is a treatment tool moving mechanism. Namely, by moving the operating wire 2 along the longitudinal axis thereof, the wire connecting link 12 is moved forward or backward with the operating wire 2, so that the operating levers 8 are rotated about the support pin 5 through the link plates 13, and thus the forceps cups 7 are opened or closed like a beak.

In this opening and closing operation, the link plates 13 and the operating levers 8 are not inched, but smoothly moved, since the link plates 13 are engaged with the rivets 18 both end portions of which are supported by the operating levers 8. Therefore, the forceps cups 7 are opened and closed in a stable manner. In an operation of the endoscope, tissue of a living body is firmly sandwiched, pinched and removed by the forceps cups 7.

As described above, according to the embodiment, the end support unit 3 can be manufactured only by press molding and does not need to use cutting processes using a milling machine. Accordingly, the manufacturing cost of the end support unit is drastically decreased and a throw-away endoscope treatment tool is easily attained, which will contribute toward the prevention of cross-infection between patients.

Figure 10:
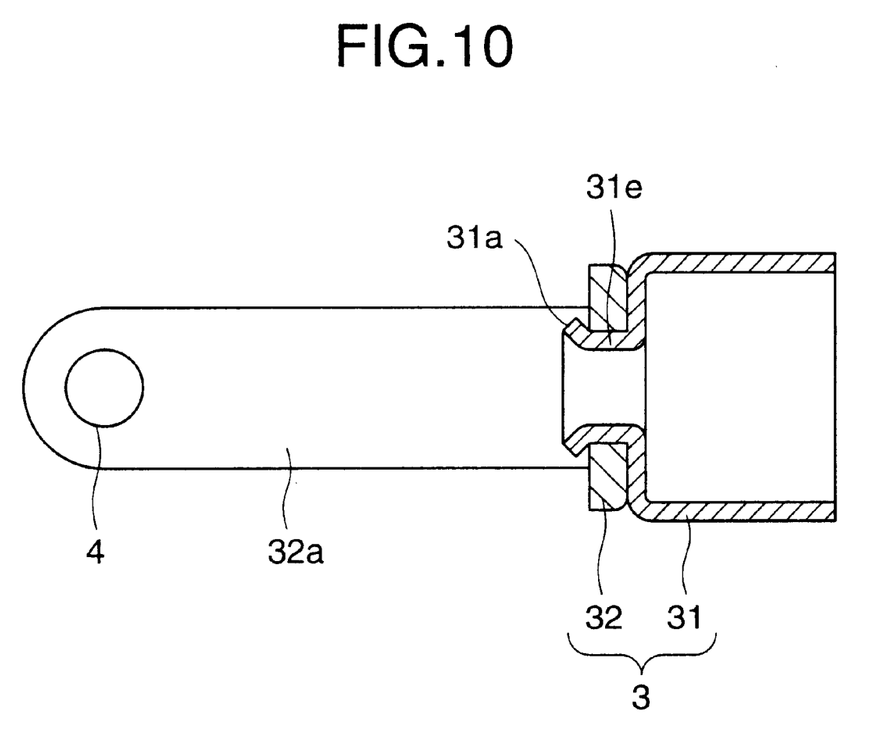
FIG. 10 is a view showing an end support unit of the other embodiment.

Note that, as shown in FIG. 10, it is possible that a tube neck portion 31e is formed in the sheath connecting cap 31 and inserted in the second hole 32d of the moving mechanism support member 32, and a projecting portion 31a of the neck portion 31e is crimped so that the sheath connecting cap 31 is connected to the moving mechanism support member 32. Further, the present invention may be applied to other treatment tool for an endoscope, other than biopsy forceps.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 11-294682 (filed on Oct. 18, 1999) which is expressly incorporated herein, by reference, in its entirety.

What is claimed is:

1. A treatment tool support device provided in an endoscope for supporting a treatment tool, said device comprising:

a moving mechanism support member having a support groove in which a treatment tool moving mechanism for moving said treatment tool is supported, said moving mechanism support member being manufactured by bending a plate in such a manner that a first planar bottom portion defining a part of said support groove is formed, said first planar bottom portion being provided with a first hole;

a sheath connecting cap provided on an end portion of a sheath, in which an operating member for driving said treatment tool moving mechanism is provided, said sheath connecting cap having a second planar bottom portion provided with second hole; and a connecting means for connecting said moving mechanism support member and said sheath connecting cap in such a manner that said first planar bottom portion and said second planar bottom portion are fixed to each other so that faces of said first planar bottom portion and said second planar bottom portion are positioned parallel to each other and said treatment tool moving mechanism and said operating member are connected through said first and second holes.

2. A device according to claim 1, wherein each of said moving mechanism support member and said sheath connecting cap is manufactured by a press molding.

3. A device according to claim 1, wherein said first planar bottom portion and said second planar bottom portion are fixed to each other by one of crimping, welding and brazing.

4. A device according to claim 1, wherein said moving mechanism support member and said sheath connecting cap are connected to each other such that said first and second holes are aligned with each other.

5. A device according to claim 1, wherein said sheath has a corrugated outer surface and said sheath connecting cap has a corrugated inner surface conforming with said corrugated outer surface.

6. The treatment tool support device according to claim 1, wherein said first planar bottom portion and said second planar bottom portion are fixed to each other so that faces of said first planar member and said second planar member are positioned parallel and abutting each other.

7. The treatment tool support device according to claim 1, wherein said moving mechanism support member and said sheath connecting cap form an end support unit, and said end support unit is configured to be removable from the sheath.

* * * * *